(12) United States Patent
Maravilla

(10) Patent No.: US 7,144,240 B2
(45) Date of Patent: Dec. 5, 2006

(54) METHODOLOGY AND APPARATUS FOR MANUFACTURING DENTAL APPLIANCES

(76) Inventor: Juanito M Maravilla, 3330 Lake Tahoe Blvd., Unit 6, South Lake Tahoe, CA (US) 96150

( * ) Notice: Subject to any disclaimer, the term of this patent is extended or adjusted under 35 U.S.C. 154(b) by 196 days.

(21) Appl. No.: 10/641,903

(22) Filed: Aug. 15, 2003

(65) Prior Publication Data
US 2004/0227266 A1 Nov. 18, 2004

Related U.S. Application Data

(60) Provisional application No. 60/470,376, filed on May 12, 2003.

(51) Int. Cl.
*A61C 13/18* (2006.01)

(52) U.S. Cl. .............. 425/178; 425/567; 425/595; 425/DIG. 11

(58) Field of Classification Search ............ 425/178, 425/180, 451.9, 567, 595, DIG. 11, 190, 425/195; 249/54; 264/16, 17, 18
See application file for complete search history.

(56) References Cited

U.S. PATENT DOCUMENTS

| | | | |
|---|---|---|---|
| 786,279 A * | 4/1905 | Franklin | ............ 425/178 |
| 3,195,185 A | 7/1965 | Goffin et al. | |
| 5,175,008 A | 12/1992 | Ueno | |
| 5,324,186 A | 6/1994 | Bakanowski | |
| 5,506,095 A | 4/1996 | Callne | |
| 6,186,761 B1 | 2/2001 | Petkow et al. | |
| 6,270,701 B1 | 8/2001 | Koroda | |
| 6,335,385 B1 * | 1/2002 | Gorlich et al. | ............ 264/17 |
| 6,488,503 B1 | 12/2002 | Lichkas et al. | |
| 6,534,562 B1 | 3/2003 | Gen et al. | |
| 2003/0111751 A1 * | 6/2003 | Monticelli et al. | ............ 264/16 |

* cited by examiner

*Primary Examiner*—Donald Heckenberg
(74) *Attorney, Agent, or Firm*—John Long

(57) ABSTRACT

The present invention is a methodology and apparatus for investment casting and injection molding of dentures. The apparatus utilizes a dental flask placed in a press held in position by a turn screw. An injector, comprised of a piston inserted into a dual open ended cylinder containing dental appliance materiel, is connected to the dental flask. A hydraulic jack presses the piston further into the cylinder to inject the dental appliance material into dental flask. To prevent contaminating contact of the dental appliance with the cylinder, the dental material is inserted first into an open ended bag that partially placed in a wire loop passing through the cylinder. As the wire loop is withdrawn from the cylinder, the open end bag is drawn into and properly oriented within the cylinder so that the open end of the bag meets the injection aperture of the dental flask.

12 Claims, 5 Drawing Sheets

METHODOLOGY AND APPARATUS FOR MANUFACTURING DENTAL APPLIANCES

CROSS-REFERENCES TO RELATED APPLICATIONS

This application claims the benefit of the Provisional Patent Application, Ser. No. 60/470,376 filed on May 12, 2003, the contents of which are relied upon and incorporated by reference.

STATEMENT REGARDING FEDERALLY SPONSORED RESEARCH OR DEVELOPMENT

Not Applicable

REFERENCE TO A "MICROFICHE APPENDIX"

Not Applicable.

BACKGROUND

1. Field of the Invention

The present invention relates to the field of injection mold methodology and apparatus for the manufacture of dental appliances such as dentures, retainers, prostheses and like dental appliances.

2. Description of the Related Art

Since the 1800s, dental appliances, such as full or partial dentures (comprised of a denture body or gum that held anchored artificial teeth), have been constructed utilizing a dental flask (mold container) which held a mold (also known as an investment) that was used to form the dental appliance. The mold is usually made from dental plaster or other suitable material and is molded around a wax model or "wax-up" of the desired dental appliance. The wax-up may include non-wax items such artificial teeth or wires in case of a retainer. The mold containing the wax-up is secured in the dental flask.

Once all the mold material in the dental flask has hardened around the wax-up, the wax-up is removed from the mold by heating the dental flask/mold. The removal of the wax-up leaves behind a cavity in the mold used to form the dental appliance. Artificial teeth, wire and the like, however, are not removed in this process and are retained into place in the mold/dental flask.

In the traditional method of forming the dental appliance, the dental flask is dissembled, and the mold opened to form two halves. Dental appliance material (such a semi-liquid or paste-like acrylic, polyurethane, or epoxy resins) is placed into the cavity portion of one of the halves. The mold and dental flask are then reassembled and compressed by vice or clamp to force the dental appliance material into all the nooks and crannies of the cavity within the mold. During this compression, excess dental appliance material is squeezed out of the two mold halves.

Steps are then taken to solidify, cure or harden the dental appliance material remaining in the mold/dental flask. During this solidification, final curing or hardening of the dental appliance material, the dental flask/mold is usually kept compressed according to the dental appliance material manufacturer's specification. Once the solidification has occurred, the clamps or vices are removed, dental flask is disassembled, and the mold is opened to release the completed dental appliance.

This traditional methodology and apparatus had several drawbacks. First and foremost was the method of placing the dental appliance material into the mold. By compressing the dental appliance material in the above-described manner, the dental appliance material would move the false teeth out of alignment as the excess dental appliance material was squeezed out of the mold. This required money consuming labor and time to correct defaults caused by this effect. Further, the presence of additional dental appliance material can cause a variety of distortions to the dental appliance itself during the formation process. This is especially true when forming partial dentures. Further, because the dental appliance material expands and shrinks during the heating and cooling of the solidification process, unless the dental appliance material is keep under constant pressure in the mold, it can cause distortions of the desired dimensions of the dental appliance. This expansion and contraction could cause porosity in the solidified dental appliance material (i.e., undesired air bubbles forming in the denture base). This porosity not only weakens the base, but causes surface roughness which is irritating to the dental appliance wearer.

To counter effect or limit the occurrence of the porosity, the traditional method of forming dental appliances relied on two clamps. The first clamp was used to make the initial compression on the dental flask/mold in squeezing the dental appliance material into place. This first clamp was then released and replaced with a specialized second clamp with spring resistance to hold the dental flask/mold together under resilient pressure. This second clamp held the dental flask/mold and were placed a container of hot water to heat the dental flask/mold for the purpose of solidifying the dental appliance material. This methodology of placing and then releasing pressure on the whole dental flask/mold potentially caused the misalignment of the dental flask/mold which results in faults in the formed dental appliance.

To overcome these and other problems of the traditional compression mold techniques for manufacturing dental appliances, there has been interest in the field toward the application of injection molding technology to the manufacture of dental appliances.

One such application is taught by U.S. Pat. No. 5,324,186 issued to Bakanowski issued on Jun. 28, 1994. This patent taught the use of a two-piece dental flask whereby the two-piece dental flask with four corners would have a bolt passing through a threaded aperture in each corner. This improvement would allow the dental flask to be tightened and held together under pressure in proper alignment. The dental flask halves also featured buttons and matching depressions to further aid in correct positioning and alignment of the mold. Each dental flask also featured vent channels for the release of any air trapped in the mold. The channels would also act as indicator when the mold was properly filled with dental appliance material (i.e., the dental appliance material would squirt out of the dental flask from the channels leading from the interior space of the mold when the mold was properly filled with dental appliance material).

For attachment of the injection equipment, the Bakanowski '186 dental flask featured threaded apertures located both on the top of each mold half and well as on the sides. The side aperture allows the connection of the injection equipment to the dental flask/mold for the forced injection of the dental appliance material into the mold.

The top threaded apertures are used for injecting mold or investment material (e.g., dental plaster) into the dental flask once the dental flask halves are assembled after filling the lower dental flask half with dental plaster. The top threaded apertures are also used to attach injection equipment so as to eject or remove the dental plaster mold from the dental flask after the two dental flasks halves have been taken apart to release the formed dental appliance.

The injection equipment is comprised of a pneumatically powered injector that is loaded with a cartridge of the dental appliance material that allows injection of dental appliance material without contamination by the operator.

There are limitations imposed on the Bakanowski '186 invention. First, the use of a two piece mold requires the cumbersome method injection of the dental mold material (dental plaster) to fill the second or top half of the flask and complete mold formation.

This injection methodology still leads to the formation of air pockets and resultant irregular surfaces on the mold impression of the dental appliance. The use of threaded apertures for injection, releasing, pressurizing and holding of the molds or dental flasks, requires the mold itself to be comprised of a certain hardness and strength to avoid stripping of the threads while under pressure. This strength and hardness requirement can lead to the limitation of materials that can be used and possibly increase construction costs for the dental flasks.

Finally, the use of a special pneumatic injection device can increase the cost of the overall system and lessen its universality.

The U.S. Pat. No. 6,187,761 issued to Petkow et al. on Feb. 13, 2001, is also an injection technology for the manufacture of dental appliances such as dentures. The Petkow '761 teaches the use of a three-piece mold, essentially a bottom dental flask portion, a top dental flask portion and a removable top cover for the top dental flask portion. This three piece dental flask avoids the problem of Bakanowski '186 invention which has to inject the dental plaster into the mold to fill the top portion or half of the dental flask. By utilizing a three piece mold, Petkow '761 can just paint on and pour in the dental plaster directly into the dental flask to form the top half of the mold.

The Petkow '761 invention further teaches the use of a compression rather than pneumatic injection of acrylic material into the mold. The Petkow '761 injection device is comprised of a cylinder with an aperture aligned with an injection aperture of the mold. The dental appliance material is then placed into the cylinder with a piston being placed over the acrylic. A locking cap and locking ring are then placed over the cylinder/piston. The mold and injector are then placed into a press which pushes down on the locking cap that causes piston to inject the acrylic into the mold. The locking ring can then engage the cylinder so as to fix the locking cap into position and thus secure the piston/dental appliance material under pressure. The pressure of the press is let off and the pressurized mold/compression device is removed for further curing of the dental appliance material in the dental flask.

The Petkow '761 invention accordingly requires a specialized pressure machine to apply the pressure to the piston to cause injection of the acrylic into the mold Another issue not addressed by the prior art is that one of the most widely used of the dental appliance materials is acrylic resin which is discolored (turns from pink to an undesirable black color, a sign of gum disease) when it comes into contact with metal, such as those found in various injection equipment.

Therefore, what is needed is an injection mold methodology and apparatus that does not utilize complicated machinery; that allows the dental flasks to be made of a variety of materials; that prevents the discoloration of acrylic resin based dental appliance materials; reduces the amount of error that can occur during dental appliance formation and enhances the accuracy of the formed dental appliance.

SUMMARY OF THE INVENTION

This invention is a simple and cost effective methodology and apparatus for using injection mold technology in the manufacture of dental appliances. This invention utilizes a multi-piece dental flask held together by multiple bolts and nuts; an injection device; and a turn screw press. The assembled dental flask is held in place against the injection device within a press utilizing a turn screw. The turn screw secures the dental flask onto the top of the injector which sits on a horizontal platform of the press.

The injector is comprised of a piston and a hollow cylinder. The hollow cylinder has an enclosed end with an aperture that axially aligns with an aperture in the dental flask. The open end of the cylinder further has an aperture for entry of the piston. This third aperture, in addition to being axially aligned with the first two apertures, is also axially aligned with a fourth aperture in the horizontal platform of the press on which the cylinder is secured.

Located on the press underneath the aperture of the horizontal platform is a hydraulic or pneumatic jack whose ram will force the piston through the aperture of the horizontal plate, piston aperture, into the interior of the cylinder.

In operation, once the dental flask/mold have been readied to receive the dental appliance material, the dental appliance material is prepared and placed in an open ended plastic bag. This bag then is placed within the interior of the cylinder of the injection device. The bag is oriented so that its open end is within the aperture of the cylinder that empties into the dental flask/mold.

The dental flask/mold, the injectors are then placed within the press and secured in position by a turn screw of the press against a horizontal plate.

In this manner, when the piston is forced into the interior of the cylinder and compresses the bag, forcing the dental appliance material into the dental flask/mold, the dental appliance material does not contact with the cylinder or the piston.

After the injection is completed, the dental flask/mold is removed from the press. A bite of dental appliance material is placed into a small open ended bag. This small bag is used as a plug for the dental flask aperture where dental appliance material was injected. A compression plate is placed over this plug and is locked onto the dental flask through the bolts and nuts securing the dental flask together. In this manner, the plug is secured under pressure so the dental appliance material in the mold can be pressurized if so desired during the curing process.

After the curing process, the dental flask is disassembled and the mold is taken apart to remove the formed dental appliance.

The invention in an alternative embodiment uses an enlarged dental flask that can accommodate a single mold containing several impressions of dental appliances so that a multitude of dental appliances could be made at the same time.

It is an object of the invention to prevent shifting of the placed positions of wire, artificial teeth and the like that are secured into the mold for incorporation into the formed dental appliance.

It is an object of the invention to avoid the need for remounting and grinding spots of the occlusal surface of the artificial teeth of the formed denture.

It is an object of the invention to avoid metal contained caused discoloration of the dental appliance material.

It is an object of the invention to lessen the time and labor needed to fit the dental appliance onto patient as well as help eliminate post-delivery pain to the patient.

It is an object of the invention to reduce that a mount of dental appliance frame work distortion that can occur during the molding and injecting process.

It is an object of the invention to increase the accuracy of molded impression of the dental appliance with the resultant accuracy of the dental appliance.

It is an object of the invention to have an injection system that can utilize a wide variety of dental appliance materials.

It is an object of this invention to be able to cast several dental appliances in a single mold.

It is an object of this invention to be able to provide easy deflasking, elimination of the distortion of dental appliance's clasp and frame, and prevent breakage of the artificial teeth in the dental appliance.

It is an object of this invention to be able to provide a dental appliance with a smooth, non-porous gum portion that is non-irritating to the patient.

It is an object of the invention to reduce the amount of wastage of dental appliance material during the formation process of the dental appliance.

DESCRIPTION OF THE NUMERICAL LISTING

Figure 1:
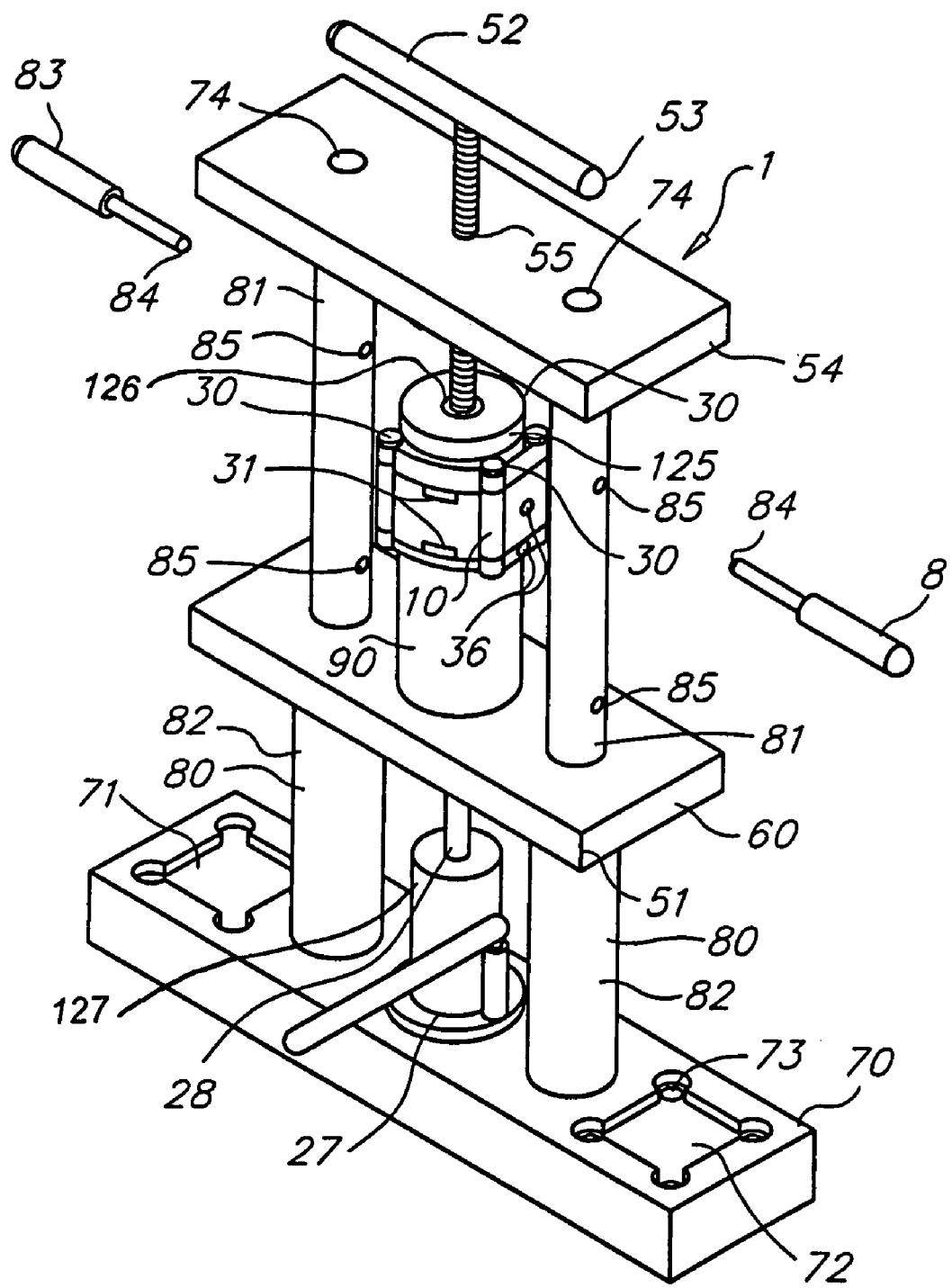
FIG. 1 A perspective drawing of the invention.
Figure 2:
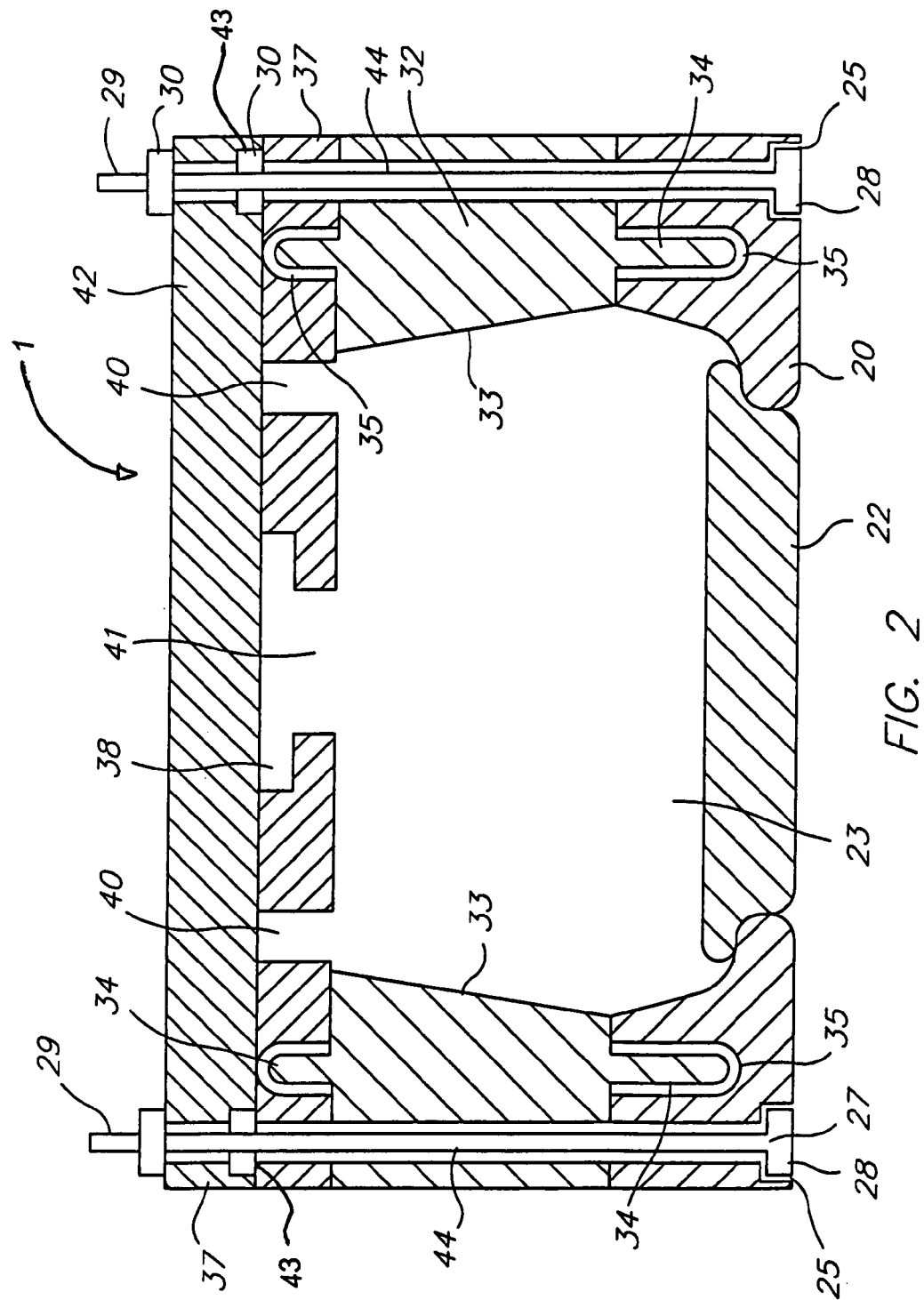
FIG. 2 A cutaway elevation view of the assembled flask.
Figure 3A:
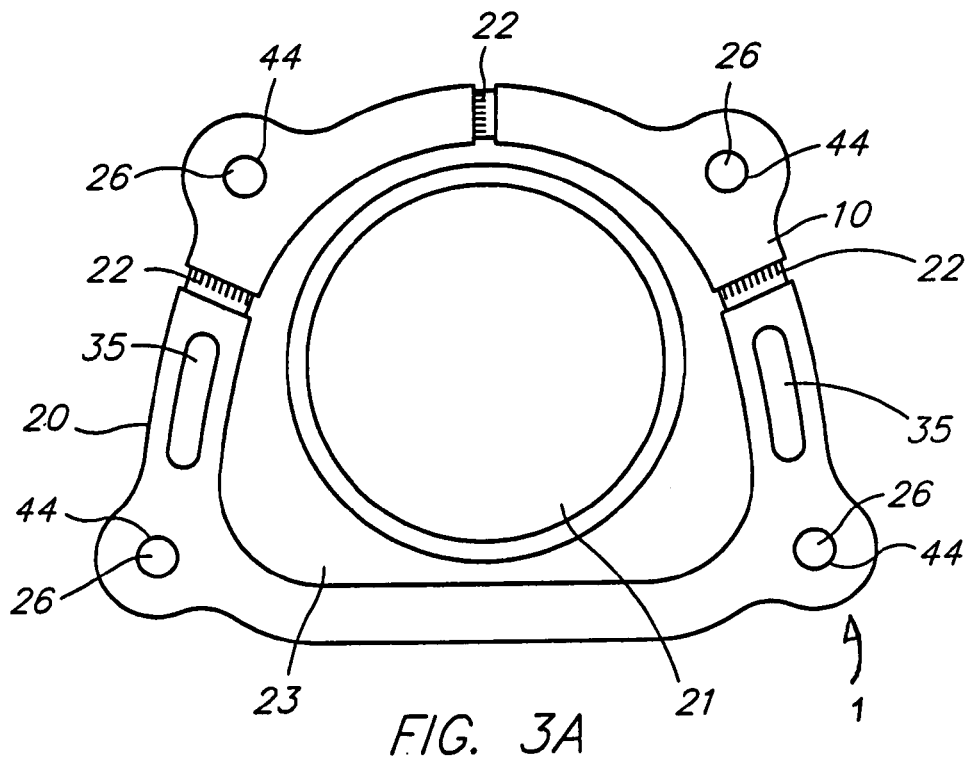
FIG. 3A A top view of the base of the flask.
Figure 3B:
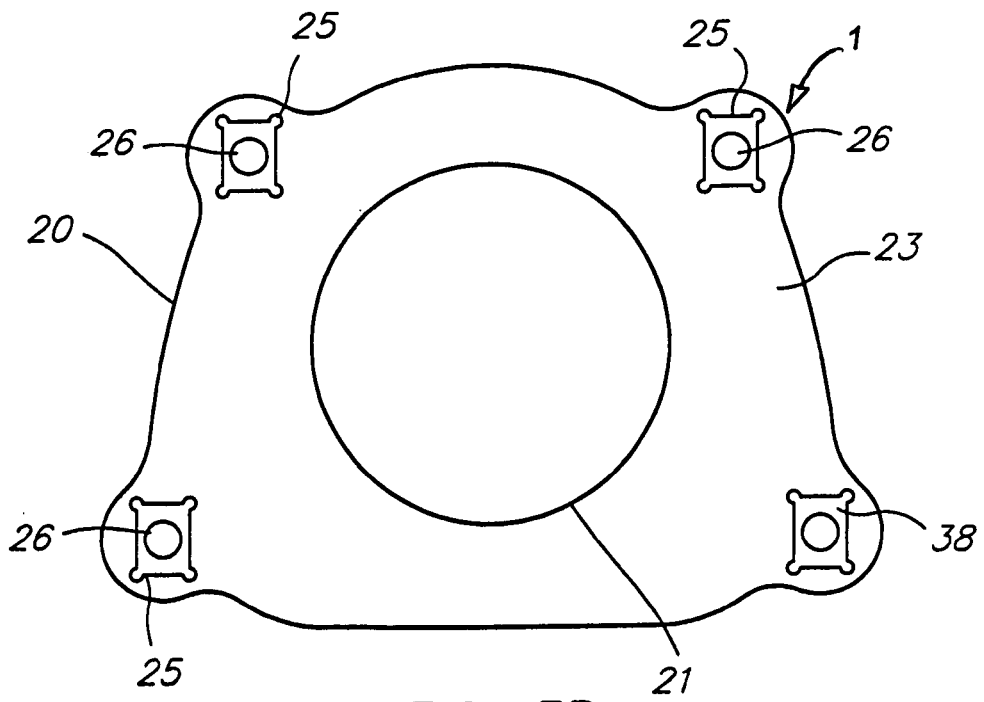
FIG. 3B A bottom view of the base of the flask.
Figure 4:
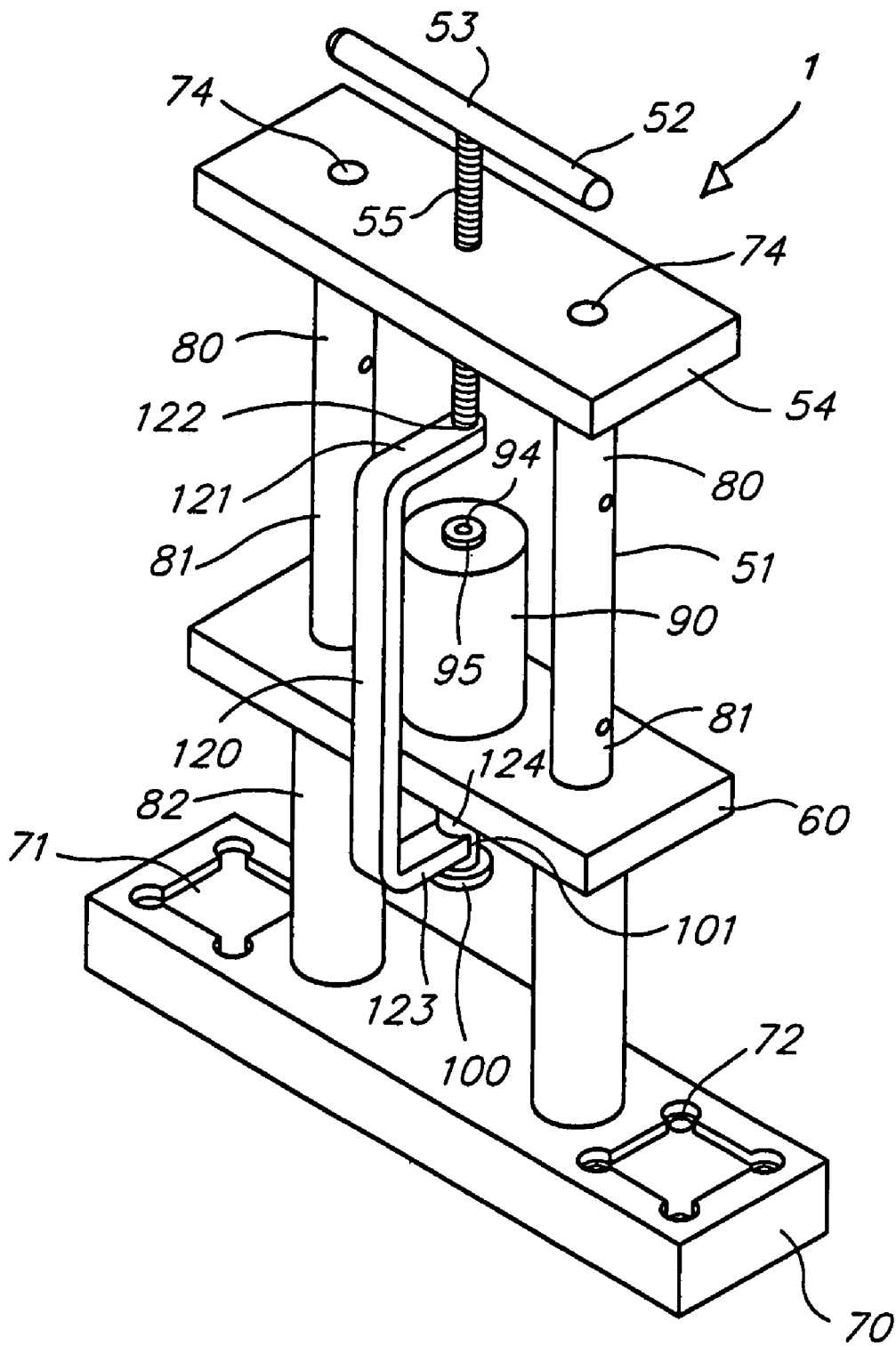
FIG. 4 A perspective view of the retractor.

1 Invention
2 Dental Appliance Material
3 Dental Appliance
4 Mold
5 Dental Appliance Impressions
10 Dental flask
20 Base
21 Knockout Plate
22 Vent Ports
23 Base Cavity
24 External Surface
25 Rectangular Depression
26 Bolt Hole
27 Bolts
28 Bolt Head
29 Threaded End
30 Nuts
31 Takedown Receptacle
32 Middle Section
33 Inner Edge
34 Guides
35 Guide Cavity
36 Retention Cavity
37 Top plate
38 Retaining Depression
40 Investment/Knockout Aperture
41 Injection Mold Aperture
42 Compression Plate
43 Compression Plate Depression
44 Bolt Channel
50 Press
51 Framework
52 Turn Screw
53 Handle
54 Top Platform
55 Threaded Aperture
60 Middle Platform
61 Injector Depression
62 Piston Aperture
70 Base Platform
71 Assembly Receptacle
72 Disassembly Receptacle
73 Bolt Exit Apertures
74 Platform Apertures
80 Vertical Stepped Pillar
81 Top Portion
82 Bottom Portion
83 Retaining pin
84 Retaining Pin End
85 Retaining Pin Aperture
90 Injector
91 Cylinder
90 Cylinder Interior
91 Cylinder Aperture
92 Injector Aperture
93 Cylinder Collar
100 Piston
101 Radial Collar
120 Retractor
121 Upper Arm
122 Screw Depression
123 Lower Arm
124 Piston Channel
125 Turn Screw Plate
126 Turn Screw Depression
127 Jack
128 Ram
129 Main Wax Sprue
131 Bag

DETAILED DESCRIPTION OF THE PREFERRED EMBODIMENTS

As shown in FIGS. 1, 2, 3A, 3B, 4, and 5, the present invention, generally denoted by numeral 1, is a methodology and apparatus for injecting dental appliance material 2 into a dental flask, generally denoted by numeral 10 containing a mold or investment 4 having one or more cavities for forming one or more dental appliances 3. In addition to the dental flask 10, the invention 1 has a press, generally denoted by numeral 50; an injector, generally denoted by numeral 90; and a jack 127.

The dental flask 10 is comprised of four parts; a base 20, a middle section 32, a top plate 37, and compression plate 42. Each part features a plurality of bolt channels 44 through which bolts 27 are inserted through the dental flask 10. Nuts 30 are used in combination with the bolts 27 to secure the parts of the dental flask 10 together.

The base 20 has a knock out plate 21 which fits into an opening in the base 20 and assists in the separation of the dental flask parts after formation of the dental appliance 3 and to aid in the release of the mold 4 from the dental flask 10. There is a plurality of vent ports 22 cut into the top of the base 20. These vent ports 10 allow air and excess dental appliance material to escape from inside of the dental flask 10 when the dental appliance 3 is being formed.

A base cavity 23 located in the base 20 holds a portion of the mold containing a wax-up and the cast of dental plaster that surrounds the exposed portion of the wax-up. The cast and the wax-up and the various methods of making same are well known to the practitioners of the art, and all of those methods are suitable for use with the various aspects of the invention 1.

In the preferred embodiment, the external surface 24 of the base 20 also features rectangular depressions 25 where the bolt holes 26 exit the base 20. These rectangular depressions 25 reversibly receive the rectangularly shaped bolt head 28. In this manner, when the nuts 25 are tightened over the threaded ends 29 of bolts 27, the rectangular depressions 25 prevent the bolts 27 from turning during tightening. Further, the rectangular depressions 25 are deep enough so that the tops of the bolt heads 28 are even with and do not protrude beyond the external surface of the base 20.

The middle section 32 has an inner edge 33 which defines the interior portion of the middle section, wherein the inner edge 33 is manufactured to match up with edges of the base cavity 23. The middle section 32 also features a multitude of guides 34 on its ends which are reversibly received by corresponding guide cavities 35 on the ends of the base 20 and the top plate 37. These guides 34 and guide cavities 35 help ensure proper alignment and orientation of the dental flask pieces during assembly.

The top plate 37 features a cylindrically shaped retaining depression 38 on its top surface to reversibly receive a corresponding cylindrically shaped collar 95 of the cylinder 91 of the injector 90. At the center of the retaining depression 38 is an injection mold aperture 41. The top plate 37 also features multiple investment/knockout apertures 40. These investment/knockout apertures 40 allow excess mold material or investment (e.g., dental plaster) to escape the dental flask 10 after the dental flask 10 has been filled with mold material and the top plate 37 is secured to the dental flask 10. These investment/knockout apertures 40 are also used to free the top plate 37 from the remaining dental flask 10 and the mold 4 after the formation of the dental appliance 3.

The threaded ends 29 of the bolts 27 are long enough to pass through the bolt holes 26 of the compression plate 42, which is placed over the nuts 30 and top plate 37, to fully engage the additional nuts 30 used to secure the compression plate 42 to the dental flask 10. The bottom surface of the compression plate 42 has compression plate depressions 43 which fit over the nuts 30 securing the top plate 37, the middle section 32 and the base 20. In this manner, the bottom surface of the compression plate 42 can rest on the top surface of the top plate 37 when the compression plate 42 is secured by additional nuts 30 secured to the threaded ends 29 of the bolts 27. As will be discussed below, the compression plate 42 is used to compress and secure a plug that blocks the injection mold aperture 41 and applies pressure to the dental appliance material 2 that has been inserted into the dental flask 10.

To aid in the disassembly of the dental flask 10 after the dental appliance(s) has/have been formed, the exterior sides of the middle section 32 have takedown receptacles 31 into which a tip of screwdriver can be inserted and twisted to force apart adjoining the top plate 37 and base 20 from the middle section 32.

To further aid in the disassembly of the dental flask 10 after the dental appliance(s) has/have been formed, both the sides of the base 20 and the middle section 32 have retention cavities 36 which reversibly receive the ends 84 of the retaining pins 83 of the press 50. These retaining pins 83 hold the middle section 32 or base 20 of the dental flask 10 in place in the press 50 while the turn screw 52 is used to eject the mold from those pieces. By using constant pressure instead of the traditional method of hammering/jarring of dental flask pieces apart, potential jarring damage to the formed dental appliance, in extracting it from the mold/dental flask, is avoided.

Once the dental flask 10 is assembled with the mold 4 inside, the dental flask 10 is placed within the press 50. The press 50 is comprised of a framework 51 and turn screw 52. The frame work 51 is comprised of three rectangular-shaped metal platforms: a top platform 54, a middle platform 60, and a base platform 70 held in horizontal parallel relationship to one another by a pair of vertical stepped pillars 80. Each platform has set of two platform apertures 74, one axially located near each end of the platform to allow for the connection to or the passage of the set of vertical stepped pillars 80.

Each of the vertical stepped pillars 80 has a stepped diameter for securing of the middle platform 60 within the framework 51 of the press 50. The vertical pillars have a top portion 81 that has a smaller sized diameter than the corresponding bottom portion 82. At the approximate midportion of each vertical stepped pillar 80 is stepped where the top portion 81 meets the lower portion 82. The top portion 81, having the same size diameter as the platform apertures 74 of the middle platform 60, passes through those apertures. This allows the middle platform 60 to rest on the step formed between the change of diameters between the top portions 81 and bottom portions 82 of the vertical stepped pillars 80.

Each of the vertical stepped pillars 80 further features a plurality of retaining pin apertures 85 that laterally traverse the top portions 81 of the vertical stepped pillars 80. The plurality of retaining pin apertures 85 of each vertical stepped pillar 80 matches in orientation and placement the retaining pin apertures 85 of the other vertical stepped pillar 80. The retaining pins 83 are inserted into and partially through a matching set retaining pin apertures 85 of the vertical stepped pillars 80 to reversibly engage the retention cavities 36 of the dental flask 10. As stated above, the retaining pins 83 hold portions of the dental flask 10 in place within the press 50 so that the turn screw 52 can force the portions of the mold 4 from portions of the dental flask 10.

The threaded aperture 55 in the middle of the top platform 54 movably engages the threaded portion of the turn screw 52. The turn screw 52 also features a handle 53 at its non-treaded end to aid the operator in applying pressure with the turn screw 52. The set of two platform apertures 74 for the top platform 54 allows for fasteners to connect the top platform 54 to the tops of the stepped vertical pillars 80.

As stated above, the set of two platform apertures 74 for the middle platform 60 allows the middle platform 60 to rest on the stepped diameter of the pair of stepped vertical pillars 80. The middle platform 60 also has a centrally located cylindrically shaped injector depression 61 that reversibly receives the base of the cylinder 91 of the injector 90. Within the center of the injector depression 61 is a piston aperture 62 of sufficient diameter to allow passage of the piston 100 of the injector 90 through the middle platform 60.

The base platform 70 has a set of two platform apertures 74 that allows partial passage of fasteners to secure the pair of stepped vertical pillars 80 to the base platform 70. The base platform 70 also has a receptacle generally located at each end of the platform that can reversibly receive and hold the base 20 of the dental flask 10. One receptacle is the assembly receptacle 71 which holds the dental flask base 10 so that the other portions of the dental flask 10 can be assembled onto the dental flask base 10. This allows the bolts 27 and nuts 30 holding the dental flask 10 together to be tightened more efficiently than if the operator held the dental flask 10 in her hand for the task.

Similarly, the other end of the base platform 70 has a disassembly receptacle 72. The disassembly receptacle 72 is similar to the assembly receptacle 71 but also includes a set of bolt exit apertures 73 which axially align with the placement of the bolts 27 of the assembled dental flask 10 when the base 20 of the assembled dental flask 10 is inserted into the disassembly receptacle 72. The bolt exit apertures 73 have sufficient diameter to accommodate the passage of the head 28 of the bolt 27. When the nuts 30 are taken off the bolts 27, a thin shaft screw driver or punch pin can be carefully applied to the top of the threaded portion 29 to push the bolts 27 through the bolts channels 44, bolt hole 26, rectangular depression 25 and the bolt exit aperture 73 so that the bolt 27 leaves the press 50 and the dental flask 10 through the underside of the base platform 70.

The injector 90 is comprised of a piston 100 and cylinder 91. The cylinder 91 has a cylindrical open ended cylinder interior 92 whose diameter closely fits the diameter of the piston 100 in order to reversibly accommodate the piston 100 that enters the cylinder interior 92 at the cylinder aperture 93. At the enclosed end of the cylinder interior 92 is an injector aperture 94 that exits at the top of the cylinder 91 in the middle of the cylinder's collar 95.

The collar 95, whose diameter closely matches the diameter of the retaining depression 38 of the top plate 37 of the dental flask 10, is reversibly received by the retaining depression 38 when the cylinder 91 is inserted in the press 50 with the assembled dental flask 10. In this manner, the dental flask injection mold aperture 41 and the injector aperture 94 are aligned to provide a generally continuous channel between the cylinder interior 92 and the open interior of the dental flask 10.

Similarly, the cylinder 91 of the injector 90 when placed within the injector depression 61 of the middle platform 60 of the press 50 allows the alignment of the cylinder aperture 93 of the cylinder 91 with the piston aperture 62 of the injector depression 61 of the middle platform 60 of the press 50, (both apertures have a diameter that closely matches the diameter of the piston 100). This overall alignment of apertures and interiors provide a generally continuous channel comprising of the injector aperture 94, the cylinder interior 92, the cylinder aperture 93, and the piston aperture 62.

In this manner, when the injector 90 is placed within the press 50, the piston 100 can be inserted through the piston aperture 62 on the underside of the middle platform 60 so as to reversibly enter the cylinder interior 92.

The piston 100 is a cylindrical plunger with a radial collar 101 cut into one end. The piston 100 has a length that exceeds the length of the cylinder interior 92 and the thickness of the middle platform 60 at the injector depression 61 combined. When the uncut end of the piston 100 is properly seated into the cylinder 91 that is fitted into the press 50, the length of the piston 100 is such that the cut end of the piston 100 will extend out to the underside of the middle platform 60.

The radial collar 101 of the piston 100 allows a retractor 120 to be attached to the piston 100 so that the power of the turn screw 52 can be harnessed to withdraw the piston 100 from the cylinder 92 after injection of the dental appliance material 3. This means of mechanical withdrawal is beneficial since the piston 100 can be "wedged" tightly into the cylinder 92 after the injector 91 has forced dental appliance material 2 under great pressure into the dental flask 10, thus making hand extraction of piston 100 very difficult, if not impossible.

The retractor 120 is a C-shaped bracket with an upper arm 121 and a lower arm 123 to allow the force of the turn screw 52, located above the middle platform 60 to be applied around and underneath the middle platform 60 to an exposed portion of the piston 100. The retractor 120 has a turn screw depression 122 at the top of the upper arm 121 of the C-shaped retractor 120 to reversibly receive at least a portion of the tip of the turn screw 52. The lower arm 123 near one side by its tip has a piston channel 124 laterally cut through it. In operation, this piston channel 124 would allow at least a portion of the lower arm 123 to reversibly engage at least a portion of the exposed piston 100 whereby the piston channel 124 would reversibly engage at least a portion of the radial collar 101 of the piston 100.

During the injection procedure when the injector 90 and the assembled dental flask 10 are properly oriented and secured within into the press 50, a turn screw plate 125 is placed on top of assembled dental flask 10 so when the turn screw 52 is turned, the tip of turn screw 52 is lowered down into the turn screw depression 126 of the turn screw plate 125. In this manner, the turn screw plate 125 helps spread the pressure exerted by the turn screw 52 over a greater area of the dental flask 10 so as to avoid unnecessary strain on a limited area of the dental flask 10 and unwanted distortion on the mold 4 inside the dental flask 10.

When the turn screw 52 has secured the dental flask 10 onto the cylinder 91 in place on the middle platform 60 and the piston 100 is in place in relation to the cylinder 91, a hydraulic or pneumatic jack 127 is then placed on the middle of the base platform 70. The jack 127 is then activated to raise its ram 128 to contact the bottom of the exposed end of the piston 100. The jack 127 is then further activated to push the piston 100 further into the cylinder 91 loaded with dental appliance material 2 to inject the dental appliance material 2 contained in a plastic open ended bag 131 into the dental flask 10. In the preferred embodiment, a standard automotive bottle-type hydraulic jack is used.

While the invention 1 is shown for usage with dental appliance material 2 of the heat cured acrylic-based resin type, the invention 1 can also be used for other types of dental appliance material 2 (e.g., microwave, room temperature, etc curing types) by altering the materials making up the dental invention 1 (i.e. non-reflective microwave materials).

Although the method described here is for making a denture for the missing teeth of a patient, it can be readily adapted for making other dental appliances 3 such as retainers for braces.

In operation, the standard method of making a dental appliance mold 4 and assembling it into a dental flask 10 is well known and readily within the knowledge of those who have ordinary skill in the art.

The first step in this method requires the operator to form alginate from prescribed compounds and place the alginate into a dental tray. The operator then presses the alginate/tray onto the gum of the patient for whom the operator is making the dental appliance. The alginate is pressed in that area of the gum where the dental appliance is to be located. The operator lets the alginate set to make an impression of the selected gum area.

The operator then uses a second alginate/tray and presses it upon those teeth that normally rest upon or oppose the missing teeth when the patient's mouth is closed.

The alginate impressions are then used to make molds for the gum portion of the dental appliance 3. A dental compound called yellow stone is poured into the alginate molds to make a representation of the selected gum area of the dental patient and its opposing teeth area. After the yellow stone has cured, it is removed from the alginate molds.

The yellow stone representations are then used to make a wax-type bite block that will fit over the selected gum area and opposing teeth area. The bite block will incorporate representations of the missing teeth and the corresponding opposing teeth.

The operator then places each representation into the mouth of the patient and has the patient close his mouth on the bite block so as to register the patient's bite location (i.e., the patient's teeth/jaw alignment in the referenced area). The wax-type bite blocks are then sealed in placed and removed from the patient.

Yellow stone compound is then put into the bite block to form a representation of the opposing teeth and gum area. The yellow stone/bite block is then set into a device called an articulator, which mimics the movement of the human jaw in reference to the upper palate of the mouth. Here, the operator unseals the bite block and commences the fitting and carving of artificial (plastic or ceramic) teeth (pontic) into that area of the bite block which represents the gum area of the missing teeth. This combination of artificial teeth and bite block is called the wax up. The articulator is then used to check the alignment and positioning of the artificial teeth against the bite block taken of the opposing teeth.

Once this is completed, the bite block with the artificial teeth (wax-up) and the corresponding yellow stone for the palate of the missing teeth are prepared for insertion into the dental flask 10. This insertion process will allow the formation of mold 4 for the gum portion of the dental appliance 3.

In the preferred embodiment of the invention 1, the means of assembling the dental flask 10 and making the dental plaster mold 4 for the dental appliance is that that the artificial teeth are placed in the lower half of the dental flask 10/mold 4 in relation to its injection position in the press. In this manner, gravity helps holds the artificial teeth in place during the fabrication of the dental appliance 3. If the dental flask 10/mold 4 are assembled/constructed so that the artificial teeth are placed in the upper half of the dental flask 10/mold 4 during the injection process, then there is a greater likelihood that the artificial teeth will fall out of place or be misaligned during the injection process. If such event occurs, the operator must spend additional time and remedial efforts to correct such defaults.

In preparing the assembly of the dental flask 10/mold 4, the operator puts in the knock out plate 21 and bolts 27 in their respective places in the base 20 of the dental flask 10. Dental plaster is mixed and placed into the base cavity 23 of the base 20. The bite block with artificial teeth and corresponding yellow stone representation of the palate are placed and secured into the top of the dental plaster held within the base cavity 23.

Once the dental plaster in the base cavity 23 has dried a specially made main wax sprue 129 is placed so that its base connects to the yellow stone casting and will be oriented to pass through the injection mold aperture 41 of the top plate 37. Additional sprue pathways made connect the wax bite block (representing the gum portion of the dental appliance impression) to the vent ports 22 leading to the outside of the dental flask 10.

A releasing agent is then sprayed over the mold, bite block, yellow stone and wax sprue held in the base cavity 23. The middle section 32 of the dental flask 10 is then placed over the base 20, orientated by the bolts 27 passing though the bolt channels 44 of the middle section 32. More dental plaster is mixed and placed into the cavity formed by the middle section 32 and the base 20. The top plate 37 is then placed over the middle section 32 with the main wax sprue 129 oriented to pass through the injection mold aperture 41 of the top plate 37. Nuts 30 are then tightened onto the threaded ends 29 of the bolts 27 passing through the top plate 37 to secure the dental flask 10 together. During this final assembly phase, any excess dental plaster will vent through the investment/knockout apertures 40 and be wiped off by the operator.

After the remaining dental plaster has cured to form the mold 4, the dental flask 10 is placed into boiling water to cause the wax of the bite block to melt. This wax is then poured out of the dental flask 10. The dental flask 10 is carefully unbolted and the mold 4 is separated into two halves (base 20 and the middle section 32/top plate 37). Boiling water is then poured onto the exposed portions of the two halves to remove any remaining wax from the cavity created by the removal of the wax bite block. A releasing agent is then applied to the areas where wax was held. The dental flask 10/mold 4 is reassembled and bolted together.

In the preferred embodiment of the invention 1, the preferred dental appliance material 2 is a heat curing acrylic resin that forms the gum portion of the dental appliance 2. This dental appliance material 2 is prepared according the specific instructions supplied by the manufacturer of the particular product and is well known to those versed in the art. As the dental appliance material 2 begins to partially cure, it will reach a solidification point called the "dough" or "snap" stage where it has "dough"-like texture and makes a "snap"-like sound when a portion of it is pulled apart.

Once the dental appliance material 2 has reached this "dough" or "snap" point in curing, the operator rolls it into a ball and places it into a cylindrical plastic bag 131 with a single open end. The bag 131 is then placed into the cylinder interior 92 by means of the cylinder aperture 93 so that the open end of the bag 131 passes through injector aperture 94 at the enclosed end of the cylinder 91. The open end of the bag 131 is then trimmed so that it reaches the top of the injector aperture 94 where it exits the cylinder collar 95.

In order to orient the bag 131 properly into the cylinder interior 92, the operator sticks long collapsed wire loop 132 through the injector aperture 94 so that the wire loop passes into the cylindrical interior 92 and out the cylinder aperture 93. The operator threads the open end portion of the bag 131 through the wire loop 132, and then much like a tailor using a needle threader to pull a thread through an eye of a needle, the operator withdraws the wire loop 132 from the injector aperture 94 bringing the open end of the bag 131 with it. This action causes the bag 131 to be pulled into the cylinder interior 92 with the open end portion of the bag 131 passing through the injector aperture 94. The dental appliance material 2 in the bag 131 prevents the bag 131 from fully passing through the injector aperture 94. At this point, the open portion of the bag 131 is trimmed accordingly.

A portion of the piston 100 is placed into the cylinder interior 92 so that the piston comes to rest upon the bag 131 containing the dental appliance material 2. The operator, ensuring the piston 100 does not fall out of the cylinder 91, thus dislodging the bag 131, places the base of the cylinder 91 of the injector 90 into the injector depression 61 of the middle platform 60. This allows the proper of alignment of the cylinder aperture 93 of the cylinder 91 and the piston aperture 62 of the middle platform 60.

The retaining depression 38 of the top plate 37 of the assembled dental flask 10 is then placed over the cylinder collar 95 of the cylinder 91 of the injector 90. In this manner, the dental flask's injection mold aperture 41 and the injector aperture 94 of the injector 90 are aligned so that there is a generally continuous interior formed by the piston aperture 62 of the middle platform 60, the cylinder aperture 93, the cylinder interior 92, injector aperture 94, mold aperture 41, and the open interior of the mold 4 held within the dental flask 10.

The turn screw plate 125 is then placed on the top of the base 20 of the dental flask 10. The turn screw 52 is then operated to lower its tip down into turn screw depression 126 of the turn screw plate 125. The turn screw should be tightly applied to the turn screw plate 125/dental flask 10/injector 90 to hold those items firmly in place within the press 50 without causing damage to these items by excessive turn screw pressure.

Figure 5:
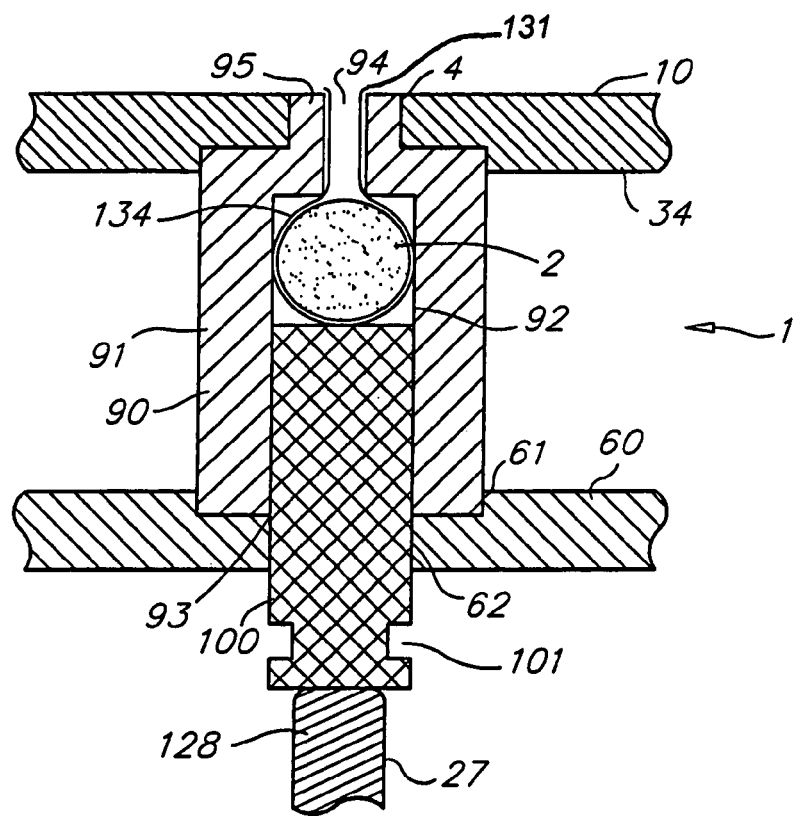
FIG. 5 A cutaway elevation of the injector in place in the press.

As shown in FIG. 5, the jack 127 is then placed on the middle of the base platform 70 and its ram 128 is raised to contact the piston 100 at the bottom of the exposed end of the piston 100. The jack 127 is then additionally activated to further propel the piston 100 into the cylinder 91. In this manner, the piston 100 contracts upon the bag 131 to inject the dental appliance material 2 or other operator selected material into the dental flask 10. Since acrylic resin reacts to metals causing the resin to turn black, the bag 131 prevents this contact within the cylinder and avoids discoloration. The bag 131, among its other benefits, makes it easy to clean up the piston 100/cylinder 91 after usage.

The operator looks for extrusion of the dental appliance material 2 from the vent ports 22 to know when the injection is complete.

After completing the injection, the turn screw 52 is operated to release the retaining pressure upon the dental flask 10 and cylinder 91. The dental flask 10 is then removed from the press 50 for final curing of the resin or other dental appliance material 2. To seal the dental appliance material 2 into the dental flask 10/mold 4, an excess amount of dental appliance material 2 is wrapped into a small portion of plastic bag 131. This wrapping is then placed over the injection mold aperture 41 of the top plate 37 of the dental flask 10. The compression plate 42 is fitted over this wrapping, the top plate 37 and the exposed threaded ends 29 of the bolts 27. Additional nuts 30 are threaded onto the bolts 27 to press the compression plate 42 onto the wrapping, tightly sealing the wrapping to act as a plug onto and into the injection mold aperture 41.

The use of the plug helps keep the dental appliance material 2 under pressure during the final curing process and limits effect of the dental appliance material 2 expansion and contraction during this period on the formation of the dental appliance 3. As stated above if pressure where not in place during this time, the expansion and contraction of the curing dental appliance material 2 would result in misalignment, porosity or unwanted surface roughness to occur in the dental appliance material 2 and the finalized dental appliance 3.

In the preferred embodiment of the invention 1, the dental flask 10 is then heated by water to cause the final curing of the acrylic resin or dental appliance material 2. As stated above, the invention 1 can be easily adapted utilizing means well known to those versed in the art for other dental appliance materials 2 that utilize other means of finalized curing.

For heating, the dental flask 10 is placed in a pot with room temperature water. The water is then heated gradually until it boils according to dental appliance material 2 manufacturer's specifications. When the dental appliance material 2 is cured and it has been allowed to cool down, the compression plate 42 and wrapping/plug are removed from the dental flask 10, and the dental flask 40 is unbolted.

The next step is the deflasking or the removal of the mold 4 (dental plaster/yellow stone) from the dental flask 10, and the removal of the dental appliance 3 (the molded gum portion and the other artificial materials such as artificial teeth or wire) from the dental flask 10. This has to be done carefully to avoid distortion or other damage to the formed dental appliance 3.

To avoid the hammering method of separation, the turn screw 52 of the press 50 is used to apply pressure to the dental flask 10 to accomplish gentle separation or deflasking. In this preferred method, a pair of retaining pins 83 is inserted into a set of matching retaining pin apertures 85 on each of the vertical stepped pillars 80 so as to reversibly engage the retention cavities 36 of the dental flask 10. In this manner, the dental flask 10 is oriented so the tip of the turn screw 52 will bear down on the knockout plate 21 of the base 20 of the dental flask 10. With the retaining pins 83 engaging the middle section 32 of the dental flask 10, the turn screw 52 presses the mold 4 from the middle section 32 and the base 20 of the dental flask 10.

At this point, the two halves of the mold 4 can be separated and the formed dental appliance 3 is removed from the mold 4. The operator using a pair of cutters or snips carefully cuts the mold material away from the dental appliance 3 to remove it from the mold half. After being freed from the mold material, the dental appliance 3 is cut away from the resin sprue formed during injection. The dental appliance is then polished before the operator applies it to the patient for final fitting and adjustment.

Figure 6:
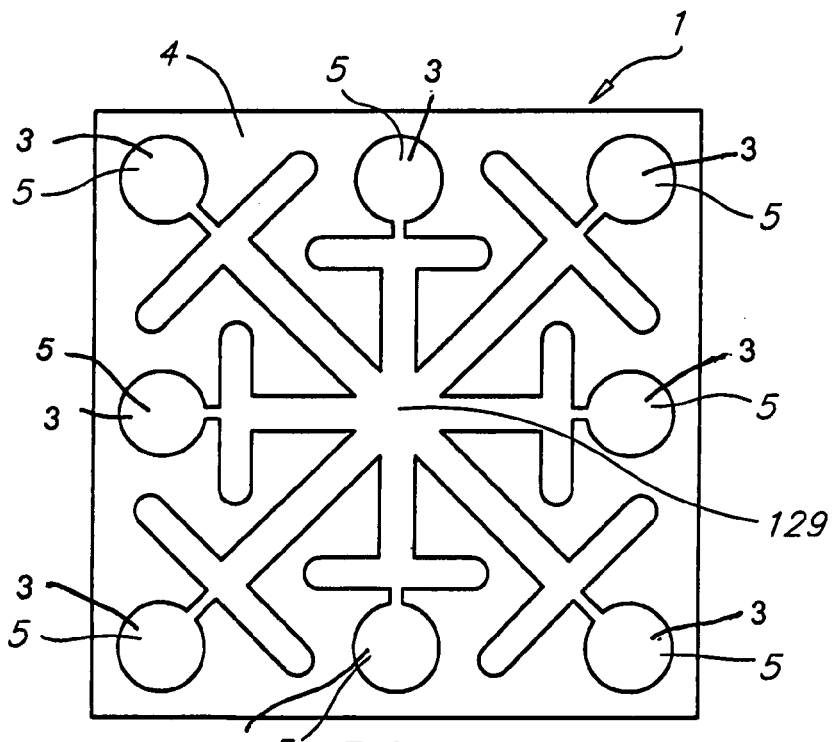
FIG. 6 A top view of representation of an alternate embodiment of the flask showing multiple dental appliance impressions with multiple sprues.

As shown in FIG. 6, another embodiment of this invention 1 would be the injection of several dental appliances 3 in one dental flask 10/mold 4. Utilizing means known to those versed in the art, the dental flask could be enlarged to contain a mold 4 holding the several dental appliance impressions 5. The size of the dental flask 10 could require additional bolt channels 44 and bolts 27 for securing the dental flask together. Further, additional sprue pathways would be needed to be laid down on the lower half of the mold 4 to connect the dental appliance impressions with the main sprue 129 leading to the injection mold aperture 41 of the top plate 37.

While these descriptions directly describe the above embodiments, it is understood that those skilled in the art may conceive modifications and/or variations to the specific embodiments shown and described herein. Any such modifications or variations that fall within the purview of this description are intended to be included herein as well. It is understood that the description herein is intended to be illustrative only and is not intended to be limitative.

I claim:

1. An apparatus for making dental appliances comprising of:
   a) a dental flask,
   b) a press,
   c) a jack,
   d) an injector,
   e) a plurality of retaining pins,
   wherein the press contains a turn screw to hold the dental flask in place within the press, wherein the injector comprises of an piston situated into a cylinder containing dental appliance material;

wherein the jack compresses the piston situated into the cylinder containing dental appliance material to inject the said dental material into the dental flask, wherein at least a portion of a plurality of retaining pins may pass through a portion of the press to engage and hold the dental flask during deflasking.

2. An apparatus for making dental appliances of claim 1, wherein the jack is hydraulically operated.

3. An apparatus for making dental appliances of claim 1, wherein the jack is pneumatically operated.

4. An apparatus for making dental appliances of claim 1, wherein the dental flask further comprises of retention cavities wherein the retention cavities may reversibly receive at least a portion of the plurality of retaining pins.

5. An apparatus for making dental appliances of claim 1, wherein the press further comprises an assembly receptacle.

6. An apparatus for making dental appliances of claim 1, wherein the press further comprises of a turn screw plate.

7. An apparatus for making a dental appliance of claim 1, wherein the dental material is ncontained in an open ended bag.

8. An apparatus for making a dental appliance of claim 7, wherein the open ended bag is plastic.

9. An apparatus for making a dental appliance of claim 1 wherein the apparatus is further comprised of a retractor.

10. An apparatus for making a dental appliance of claim 9 wherein the retractor is U-shaped and is comprised of an upper arm with a screw depression and a lower arm with a piston channel.

11. An apparatus for making dental appliances of claim 1, whereinat least a portion of the plurality of retaining pins pass through apertures in the press.

12. An apparatus for making dental appliances of claim 1, wherein the press further comprises an assembly receptacle.

* * * * *

UNITED STATES PATENT AND TRADEMARK OFFICE
Certificate

Patent No. 7,144,240 B2                                                            Patented: December 5, 2006

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Juanito M. Maravilla, South Lake Tahoe, CA (US); and Mercedes H. Maravilla, South Lake Tahoe, CA (US).

Signed and Sealed this Nineteenth Day of October 2010.

*JOSEPH S. DEL SOLE*
*Supervisory Patent Examiner*
*Art Unit 1791*
*Technology Center 1700*